(12) United States Patent
Benson

(10) Patent No.: US 6,799,122 B2
(45) Date of Patent: Sep. 28, 2004

(54) METHOD FOR IDENTIFYING POLYMORPHIC MARKERS IN A POPULATION

(75) Inventor: Andrew K. Benson, Lincoln, NE (US)

(73) Assignee: Conagra Grocery Products Company, Irvine, CA (US)

( * ) Notice: Subject to any disclaimer, the term of this patent is extended or adjusted under 35 U.S.C. 154(b) by 124 days.

(21) Appl. No.: 09/945,564

(22) Filed: Aug. 31, 2001

(65) Prior Publication Data

US 2003/0048934 A1 Mar. 13, 2003

(51) Int. Cl.$^7$ ................................................ G06F 17/00
(52) U.S. Cl. .............................................. 702/20; 435/6
(58) Field of Search .............................. 702/20; 435/6; 707/100, 104.1

(56) References Cited

U.S. PATENT DOCUMENTS 6,223,127 B1    4/2001    Berno .......................... 702/19

FOREIGN PATENT DOCUMENTS

WO    PCT WO 95/11995    5/1995

OTHER PUBLICATIONS

Gingeras et al. "Simultaneous Genotyping and Species Identification Using Hybridization Pattern Recognition Analysis of Generic Mycobacterium DNA Arrays" Cold Spring Harbor Laboratory Press vol. 8, No. 4: 435–448 (1998).
Behr et al. "Comparative Genomics of BCG Vaccines by Whole–Genome DNA Microarray" Science 284: 1520–1523 (1999).
Eisen et al. "Cluster analysis and display of genome–wide expression patterns" Proc. Natl. Acad. Sci. 95: 14863–14868 (1998).
Eisen "Cluster and Tree View" Manual: 20 pages (1998–99).
Ferea et al. "Systematic changes in gene expression patterns following adaptive evoluiton in yeast" Proc. Natl. Acad. Sci 96: 9721–9726 (1999).
Fitzgerald et al. "Evolunionary genomics of Staphylococcus aureus: Insights into the origin of methicillin–resistant strains and the toxic shock snyndrome epidemic" Proc. Natl. Acad. Sci 98: 8821–8826 (2001).
Lashkari et al. "Yeast microarrays for genome wide parallel genetic and gene expression analysis" Proc. Natl. Acad. Sci 94: 13057–13062 (1997).
Salama et al. "A whole–genome microarray reveals genetic diversity among Helicobacter pylori strains" Proc. Natl. Acad. Sci 97: 14668–14673 (2000).

Primary Examiner—James Martinell
(74) Attorney, Agent, or Firm—Nutter McClennen & Fish LLP

(57) ABSTRACT

A method is provided for the identification of polymorphic markers in a population. The method includes genotypically characterizing a first sample of a population, selecting one or more individuals of the first sample based upon the genotypic characterization, fabricating a microarray with genomic DNA from each individual selected, and genotyping a second sample of the population using each fabricated microarray as a reference, thereby identifying the polymorphic markers in the population. Also provided is a method for the identification of polymorphic markers in a bacterial population. The method includes phenotypically characterizing a first sample of a population, selecting one or more individuals of the first sample based upon the phenotypic characterization, fabricating a microarray with genomic DNA from each individual selected, and genotyping a second sample of the population using each fabricated microarray as a reference, thereby identifying the polymorphic markers in the population. Also provided is a method for identifying unique bits among a plurality of bit strings including providing a plurality of bit strings, wherein each string has the same number and position of bits, and each bit has a value of 0 or 1, generating a graphical representation—including selectable elements—representing the relatedness of the bit strings, making a selection of a first selectable element, making a selection of a second selectable element, and identifying bits that are present in each bit string represented by the first selectable element and absent in each bit string represented by the second selectable element, or vice-versa.

14 Claims, 2 Drawing Sheets

METHOD FOR IDENTIFYING POLYMORPHIC MARKERS IN A POPULATION

BACKGROUND OF THE INVENTION

1. Field of the Invention

This invention relates generally to the fields of population and molecular genetics. In particular, it relates to a method for identifying polymorphic markers in a population.

2. Related Art

As a general rule, the taxonomic classification of species is generally reserved for organisms that are genetically similar and capable of mating productively. Since bacteria are asexual organisms, species generally refers to populations that share genetic and biochemical similarity. Despite the fact that species of bacteria share similarity, significant diversity can be observed when comparing different populations of a given species. To illustrate, the gut bacterium *Escherichia coli* consists of approximately 170 different serotypes.

One of the most important tasks of a clinical or industrial microbiologist is the precise determination of what microorganism, if any, is present in a sample. Using some commonly known and simple techniques, the microbiologist can generally deduce the species of the unknown microorganism relatively quickly. However, subspecies or actual strain determination of the microorganism present in the sample frequently requires sophisticated methods of genetic or biochemical analysis. This, of course, translates into higher costs and a slower turnaround time.

Determination of a specific strain of bacteria rather than the mere species that is present in a sample is particularly important to the food industry. For example, of the approximately 170 strains of *E. coli*, only about 30 of them are pathogenic to humans. Depending on the pathogenic potential of strains or subspecies, processors may often elect to dump a batch contaminated with the species rather than invest time and effort in determining the precise strain or subspecies classification. This is because of the aforementioned costs associated with deducing the actual strain to determine if it is in fact pathogenic. The obvious problem with such "dumping" is that it also has costs associated with it, namely lost revenues. Therefore, it is desirable to have some method of quickly identifying what strain of bacteria may be present in a sample. In order to develop diagnostic tools for the rapid identification of bacterial strains, it is first necessary to identify genetic markers which are characteristic of problematic and less problematic strains.

In addition to the practical application of strain-level classification, understanding genetic characteristics of populations of bacteria is also important for creating safer food environments. Alteration of the genome by gene acquisition, deletion, and mutation, along with new routes of transmission into the food chain, and the selective pressures that are imposed in food production environments, are the elements that drive evolution and emergence of foodborne pathogens. Thus, it increasingly important that new methods are devised for understanding how pathogenic and spoilage organisms enter the food supply, how different populations of pathogenic organisms are effected by selective pressures in food production environments, and how this relates to characteristics that confer increased virulence, spoilage, and/or transmissibility on certain populations. Several molecular genetic approaches have been developed to provide high-resolution information about populations, including random amplified polymorphic DNA (RAPD), amplified fragment length polymorphism (AFLP), octamer-based genome scanning (OGBS), and multi-locus sequencing. Each of these approaches suffers from the fact that they provide only limited coverage of the genome in a single experiment and must therefore be performed in a plurality of intentions to increase genome coverage, particularly in the case of closely related strains. The present invention overcomes this limitation by allowing for coverage of the entire genome in a single experiment and by determination of genetic segments that are specific to relevant populations.

Another bacterial of particular interest to the food industry is *Listeria monocytogenes*. Although several serotypes of *Listeria monocytogenes* strains are found in foods and in the environment, most human infections (>95%) are caused by only three serotypes, 1/2a, 1/2b and 4b. These strains belong to two major genetic groups, one of which includes serotype 1/2a while 1/2b and 4b belong to the other group. Most molecular genetic and immunologic studies have used strains from the first genetic group, including 1/2a (strains 10403s, EGD, NCTC7973 Mack) and 1/2c (strains LO28). Strains representing the other group have largely been omitted from molecular genetic studies. However, strains from this group, especially strains of serotype 4b, may be of the most significance to the food industry and public health.

Strains of serotype 4b account not only for a substantial fraction (ca. 40%) of sporadic infections but also for almost all of the common-source outbreaks of listeriosis that have been studied, including the 1985 Jalisco cheese out break in Los Angeles and the latest multi-state outbreak in the United States traced to contaminated hot dogs. There is a need for a relatively quick, simple, and inexpensive method for determining unique DNA sequence information for rapidly distinguishing among different subpopulations of *L. monocytogenes* isolates. Such tests are crucial for high-throughput analyses necessary for epidemiological studies and risk assessment studies.

*Listeria monocytogenes* is a ubiquitous gram-positive organism that can cause life-threatening infections ranging from meningitis, septicemia, and fetal death. Although the incidence of listeriosis is low, the associated morbidity can be quite high, particularly in pregnant women and immunocompromised individuals (Gellin and Broome, 1989).

*L. monocytogenes* is well known for its robust physiological characteristics and is one of few pathogenic bacteria capable of growth at refrigeration temperatures, under conditions of low pH, and/or high osmolarity (Farber and Brown, 1990; Farber and Pterkin, 1991; Kroll and Patchett, 1992; Miller 1992; Wilkins et al. 1972). Kroll and Patchett, 1992).

*L. monocytogenes* can grow in several types of cultured cells and is capable of intracellular growth and spread to adjacent host cells through the use of host cell cytoskeletal components (Galliard et al. 1987; Portnoy et al. 1988; Tilney and Portnoy, 1989; Mounier et al. 1990). Genetic analysis of virulence in *L. monocytogenes* has identified several loci that contribute directly to the series of events that occur during host cell invasion (reviewed in Portnoy et al. 1992, Sheehan et al. 1994). These virulence genes include adhesins, a cytolytic toxin, an actin polymerizing protein and phospholipases, that function in host cell entry, vacuole escape, replication, and spread to adjacent host cells respectively.

Several signals, such as temperature and carbohydrates seem to control regulation of the virulence genes (Leimeister-Wachter et al. 1992; Park and Kroll, 1993) and recent evidence suggests that these are separate pathways that govern expression of the virulence genes (Renzoni et al.

1997). Thus, the virulence gene regulator, called PrfA, may couple transcription of the virulence genes to a variety of cues that could signal entry into a host.

L. monocytogenes* strains display serotypic differences in somatic (numbered) and flagellar (lettered) antigens (Seelinger and Hoehne, 1979). Although 13 different serotypes of *L. monocytogenes* are found in foods and in the environment (Farber and Pterkin, 1991), most clinical isolates are of only 3 serotypes, 1/2a, 1/2b and 4b (Schuchat et al. 1991), suggesting that these serotypes may be particularly virulent for humans or are better able to survive the necessary hurdles for transmission and establishment of infection.

Several studies have been conducted to examine genetic relationships among *L. monocytogenes* strains. One of the most significant was an early study using Multi-Locus Enzyme Electrophoresis (MLEE), which identified 45 different electropherotypes (ETs—combinations of alleles or protein isomorphs) that were divided amongst two distinct genetic lineages (Piffaretti et al. 1989). Perhaps one of the more striking results from this study was the finding that nearly all of the strains isolated from large outbreaks comprised only 2 ETs, suggesting that these clones may be highly virulent for humans. In contrast to the clustering of the epidemic strains, strains isolated from sporadic cases were dispersed among many different ETs.

In addition to MLEE, investigators using pulsed-field gel electrophoresis (Brosch et al 1994), ribotyping (Graves et al. 1994), RFLP analyses of virulence genes (Vines et al. 1992), and DNA sequence analysis of virulence genes (Gutekunst et al. 1992 and Rasmussen et al. 1991) have also demonstrated the existence of two distinct lineages of *L. monocytogenes* strains. Recent studies of Rasmussen et al. (1995) and Wiedmann et al. (1997) using multilocus sequence analysis of different combinations of virulence-associated genes along with RFLP analyses and ribotyping independently demonstrated the existence of a third lineage of *L. monocytogenes*. Genetic relationships demonstrated by these methods showed that epidemic strains were confined to lineage I, sporadic strains were found in lineage I and II, while lineage III was devoid of human clinical isolates (Wiedmann et al. 1997). In fact, the genetic distinctiveness lead these authors to propose that lineage III strains are largely animal pathogens and should be designated as a new species of Listeria (Wiedmann et al. 1997). Together, these studies, which have employed several different means of genetic analysis, strongly support the notion that virulence, or physiological characteristics that facilitate survival of hurdles necessary to establish infection, are not evenly distributed among the lineages of *L. monocytogenes*. Studies of several different bacterial pathogens have, in fact, demonstrated that clonal expansion of highly virulent subpopulations, marked by unique combinations of virulence gene alleles, is usually associated with increased spread of disease (see, e.g. Karaolis et al. 1995, Musser and Krause, 1998, reviewed in Musser, 1996). Recently it has been shown that even within apparently clonal populations of *E. coli* O157:H7, divergent subpopulations exist in the U.S. and appear to have unique ecologies (Kim et al. 1999). Therefore, the phenomenon of variation in virulence potential appears to be a general characteristic of pathogenic microorganisms.

There are several possibilities, which are not mutually exclusive, that could account for differences in virulence characteristics of *L. monocytogenes* subpopulations. One of the simplest explanations is that the putative more virulent subpopulations carry particular combinations of virulence gene alleles that render the strains better able to penetrate host cells and tissues. In other pathogenic species, allele combinations of virulence genes appear to play an important role in the rise and spread of certain clones. Secondly, it is possible some lineages may possess additional genes that contribute to virulence or that they possess unique patterns of virulence gene expression. Strain-specific variations in the modulation of PrfA activity have recently been demonstrated with respect to carbon-source effects on prfA-dependent gene expression in different *L. monocytogenes* strains (Brehm et al. 1999; Huilett et al. 1999). Lastly, it is also possible that physiological difference among the lineages confers characteristics that make certain lineages better able to survive the necessary hurdles to establish infection.

SUMMARY

A method is provided for identifying polymorphic markers in a population comprising genotypically characterizing a first sample of the population, selecting one or more individuals of the first sample based upon the characterization, fabricating a microarray with genomic DNA from each selected individual, genotyping a second sample of the population using each fabricated microarray as a reference, identifying the polymorphic markers in the population, and sorting the markers to identify those characteristic of the population of interest. In one embodiment, the population is a bacterial population. The bacterial population is selected from the group consisting of *Listeria monocytogenes, Escherichia coli, Lactobacillus casei, Lactococcus lactus, Salmonella typhimurium, Salmonella enteredítis*, and *Salmonella typhi*.

Also provided is a method for identifying polymorphic markers in a bacterial population comprising phenotypically characterizing a first sample of the population, selecting one or more individuals of the first sample based upon the characterization, fabricating a microarray with genomic DNA from each selected individual, genotyping a second sample of the population using each fabricated microarray as a reference, identifying the polymorphic markers in the population, and sorting the markers to identify those characteristic of the population of interest. In one embodiment, the bacterial population is selected from the group consisting of *Listeria monocytogenes, Escherichia coli, Lactobacillus casei, Lactococcus lactus, Salmonella typhimurium, Salmonella enteredítis*, and *Salmonella typhi*.

Also provided is a method for identifying unique bits among a plurality of bit strings including providing a plurality of bit strings wherein each bit string has the same number and position of bits and wherein each bit has a value of 0 or 1, generating a graphical representation—including selectable elements—representing the relatedness of the bit strings, making a selection of a first selectable element, making a selection of a second selectable element, and identifying bits that are present in each bit string represented by the first selectable element and absent in each bit string represented by the second selectable element, or vice-versa. In one embodiment, the relatedness of the bit strings is determined by the commonality of bit values at corresponding positions in the bit strings. In both the method and the embodiment of the method, the graphical representation can be a dendrogram and the selectable elements can be leaves and nodes, each leaf representing a single bit string, and each node representing two or more bit strings.

Also provided is a computer readable medium having software for identifying unique bits among a plurality of bit strings, including logic configured to provide a plurality of bit strings, each string having the same number and position of bits, each bit having a value of 0 or 1, logic configured to generate a graphical representation, including selectable elements, representing the relatedness of the bit strings, logic configured to make a selection of a first selectable element, logic configured to make a selection of a second selectable element, and logic configured to identify bits that are present in each bit string represented by the first selectable element and absent in each bit string represented by the second selectable element, or that are absent in each bit string represented by the first selectable element and present in each bit string represented by the second selectable element. In one embodiment, the relatedness of the bit strings is determined by the commonality of bit values at corresponding positions in the bit strings. In both the method and the embodiment of the method, the graphical representation can be a dendrogram and the selectable elements can be leaves and nodes, each leaf representing a single bit string, and each node representing two or more bit strings.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention.

DETAILED DESCRIPTION OF THE PREFERRED EMBODIMENTS

Figure 1:
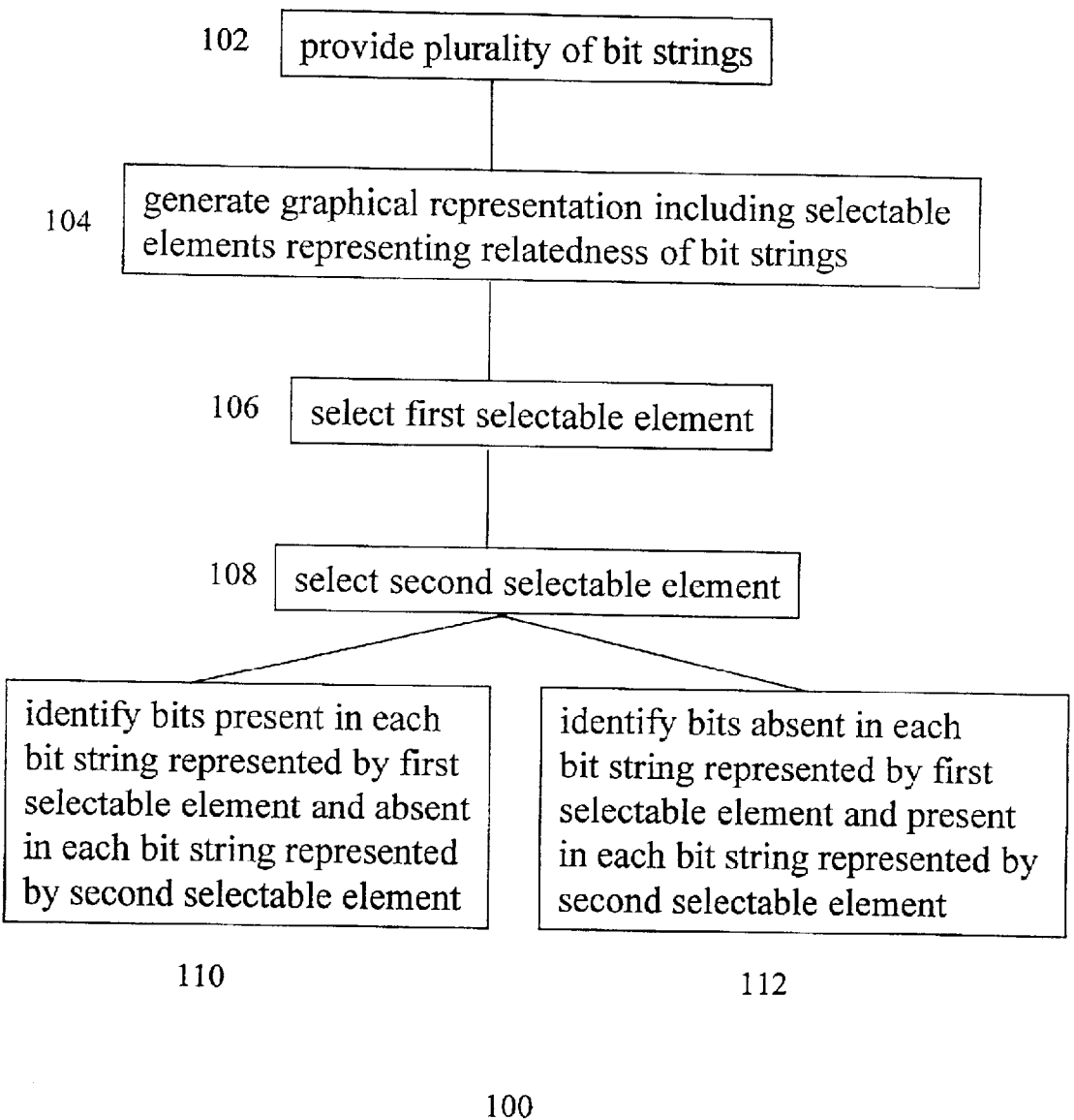
FIG. 1 is a flow chart illustrating the operation of software for identifying unique bit strings among a plurality of bit strings.

It is to be understood that the invention described herein is only illustrative. None of the embodiments shown herein are limiting. It would be apparent to those skilled in the art that modifications and adaptations can be made without departing from the scope of the invention as defined by the claims appended.

The present invention provides a method for the identification of polymorphic markers in a population.

As used herein, "population" is intended to refer to two or more organisms belonging to the same species. A "sample" of a population can include the entire population or any portion thereof.

As used herein, "marker" is intended to refer to a feature that is capable of distinguishing one individual or member from another individual or member in a sample.

The inventive method includes the steps of genotypically characterizing a first sample of a population, selecting one or more individuals of the first sample based upon the genotypic characterization, fabricating a microarray with genomic DNA from each individual selected, genotyping a second sample of the population using each fabricated microarray as a reference, identifying the polymorphic markers in the population, and sorting the markers to identify those characteristic of the population of interest.

Typically, the microarray is a linear or two-dimensional array of regions, formed on the surface of a solid support, having a density of discrete regions of at least about 100/$cm^2$, and preferably about 1000/$cm^2$. The regions in such microarrays have typical dimensions, e.g., diameters, in the range of about 10–250 $\mu$m, and are separated from other regions in the array by about the same distance. DNA microarrays can be fabricated by deposition of a set of synthetic oligonucleotides, PCR products, or other forms of genetic material onto the regions of the solid support, such as a silicanated glass slide.

Depending on the size of the genome of the organism of interest, the size of the solid support, and the distance separating the discrete regions, a DNA microarray can be fabricated such that the entire genome is present. Whole genome microarrays containing PCR products derived from the entire genome are fabricated by two general methods. First, if the genome sequence of the organism of interest is available, individual oligonucleotide primer combinations are designed for each coding region in the genome, allowing for the amplification by polymerase chain reaction (PCR) of each gene in independent reactions. The amplification products are then used to fabricate the microarray. If the genome sequence is not available, then a "shotgun" approach is used. In this approach, a library of the genomic DNA is constructed by cloning segments into a vector containing common priming sites adjacent to the cloning site. Each clone from the library is then independently amplified and the amplicons used to fabricate the microarray. Deposition or "printing" of the oligonucleotides onto the solid support can be accomplished by any one of several methods known in the art, such as by an automated arrayer. Regardless of the method that is used to deposit the oligonucleotides onto the solid support, the user should be able to trace the oligonucleotides at a given region back to its original clone.

The method of the invention is useful for the identification and sorting of polymorphic genetic markers in a population of any living organism including, in a preferred embodiment, a bacterial population. Representative bacterial populations include *Listeria monocytogenes, Escherichia coli, Lactobacillus casei, Lactococcus lactus, Salmonella typhimurium, Salmonella entereditis*, and *Salmonella typhi*.

Genotypic Characterization of First Sample

A first sample of the population can be genotypically characterized using any suitable method. Useful methods include, but are not limited to, whole genome microarrays, random amplified polymorphic DNA (RAPD), amplified fragment length polymorphism (AFLP), multi-locus enzyme electrophoresis (MLEE), octamer-based genome scanning (OBGS), and multi-locus sequence typing (MLST). For genotypic characterization in the present invention, it is preferable to use whole genome microarrays. This is accomplished by fabricating a microarray with genomic DNA from a representative of a first sample, and then genotyping the individual(s) present in the first sample using the microarray of the representative as a reference.

Preferably, the genotyping step is performed individual-by-individual. For each individual that is genotyped, a predetermined, equivalent amount of genomic DNA from both the representative and the individual is labeled with a fluorescent dye, and then hybridized to the microarray. Due to complementarity of sequence, the DNA from the representative will hybridize to all of the oligonucleotides present in each region of the microarray. As such, a different label is used during labeling of the representative's DNA and the individual's DNA.

Following hybridization, fluorescence intensities registered by hybridization of the labeled DNA from the representative and the individual to each region of the microarray are determined by a multicolor, microarray scanner and converted to binary elements or whole integers through image analysis and statistical analysis software. The image analysis software creates an output of the fluorescence intensities, in a spreadsheet file, representing all of the regions of the microarray. For the statistical analysis, it is preferable to use binary conversion to create a bit string representing the pattern of hybridization of the individual's DNA to the microarray regions. Binary conversion is performed by comparing the hybridization intensity of each region on different dye channels. If the individual's DNA contains a hybridizing segment, the ratio of hybridization intensities of the representative's DNA to the individual's DNA is or is nearly one. If the individual's DNA lacks the segment, or if the segment is substantially altered, the ratio is much higher. A threshold of ratios is used such that, preferably, a binary bit of 1 is assigned to the region if the ratio of hybridization intensities is <2 standard deviations above the mean, and a binary bit of 0 is assigned to the region if the ratio is >2 standard deviations above the mean, although it would be readily apparent to one of ordinary skill in the art that these numbers could be reversed. The resulting output file is rendered in text format, although it can also be rendered in spreadsheet format. The output file can contain either converted binary elements or normalized ratios. The statistical analysis software, preferably PERL-based, combines the data from each output file for each individual into a composite file, and performs statistical analysis by normalization of the data through mean and median centering of the ratios. Once the composite file is generated, a determination is made as to the genetic relatedness of the individuals present in the first sample. Such a determination is made by inputting the composite file, preferably containing a bit string corresponding to each individual from the first sample, into a separate computer program containing one or more clustering algorithms. Preferably, the clustering program contains both neighbor joining and bootstrap algorithms. The clustering program is directed to render a dendrogram made up of each individual in the first sample. Such a dendrogram reveals the relative genetic distance between each individual, as well as the existence of genetically related groups or clusters among the individuals. It would be obvious to one skilled in the art that clustering can be performed upon either binary or integer measurements from the array.

Selecting One or More Individuals of First Sample Based Upon Genotypic Characterization Once the first sample is genotypically characterized, one or more individuals present in the first sample are selected based upon the genotypic characterization. The selection is performed such that each individual selected shares the most characters among the other individuals of the same group or cluster.

Fabricating Microarray from Each Individual Selected from First Sample

Once one or more individuals of the first sample are selected, a whole genome microarray is prepared from each.

Genotyping Second Sample

Once whole genome microarrays are prepared from each individual selected from the first sample, a second sample of the population is genotyped using each selected individual's microarray as a reference. Preferably, this is performed member-by-member. For each member of the second sample that is genotyped, a predetermined amount of genomic DNA from each of the selected individual(s) and the member is labeled with a fluorescent dye, and then hybridized to the respective microarray(s). Due to complementarity of sequence, the DNA from the selected individual will hybridize to all of the oligonucleotides present in each region of the respective microarray. As such, a different fluorescent dye is used during labeling of the selected individual's DNA and the member DNA.

Following hybridization, fluorescence intensities registered by hybridization of the labeled DNA from the selected individual and the member to each region of the respective microarray are determined by a multicolor, microarray scanner and converted to binary elements or whole integers through image analysis and statistical analysis software. The image analysis software creates an output of the fluorescence intensities, in a spreadsheet file, representing all of the regions of the microarray. For the statistical analysis, it is preferable to use binary conversion to create a bit string representing the pattern of hybridization of the member's DNA to the microarray regions. Binary conversion is performed by comparing the hybridization intensity of each region on different dye channels. If the member DNA contains a hybridizing segment, the ratio of hybridization intensities of the selected individual's DNA and the member's DNA is or is nearly one. If the member DNA lacks the segment, or if the segment is substantially altered, the ratio is much higher. A threshold of ratios is used such that, preferably, a binary bit of 1 is assigned to the region if the ratio of hybridization intensities is >2 standard deviations above the mean, and a binary bit of 0 is assigned to the region if the ratio is <2 standard deviations above the mean. The resulting output file is rendered in text format, although it can also be rendered in spreadsheet format. The output file can contain either converted binary elements or normalized ratios. The statistical analysis software, preferably PERL-based, combines the data from each output file for each member into a composite file, and performs statistical analysis by normalization of the data through mean and median centering of the ratios. Once the composite file is generated, a determination is made as to the genetic relatedness of the members present in the second sample. Such a determination is made by inputting the composite file, preferably containing a bit string corresponding to each member from the second sample, into a separate computer program containing one or more clustering algorithms. Preferably, the clustering program contains both neighbor joining and bootstrap algorithms. The clustering program sorts and groups the data contained in the composite file, while preserving the information concerning the identity of the microarray region corresponding to each bit. The clustering program is directed to render a dendrogram made up of each member of the second sample. Such a dendrogram reveals the relative genetic distance between each member, as well as the existence of genetically related groups or clusters among the members. Phylogeny may also be inferred from the dendrogram. It would be obvious to one skilled in the art that clustering can be performed upon either binary or integer measurements from the array.

Once the members of the second sample are grouped into genetically related groups or clusters, the clustering program is directed to select two such groups or clusters. The clustering program is then directed to identify markers, corresponding to particular microarray regions, that are present in one group or cluster, and absent in another. The program can also be directed to identify markers that are present in at least one member of one group or cluster and absent in all the members of the second group or cluster.

Since the information concerning the micorarray region corresponding to each bit is preserved during the sorting and grouping process, microarray regions can be easily identified showing these types of markers. These particular regions can then be identified on the original microarray fluorescence scans.

Also provided is a method for the identification of polymorphic markers in a bacterial population. The inventive method includes phenotypically characterizing a first sample of a population, selecting one or more individuals of the first sample based upon the phenotypic characterization, fabricating a microarray with genomic DNA from each individual selected, and genotyping a second sample of the population using each fabricated microarray as a reference, thereby identifying the polymorphic markers in the population. Representative bacterial populations include *Listeria monocytogenes, Escherichia coli, Lactobacillus casei, Lactococcus lactus, Salmonella typhimurium, Salmonella entereditis*, and *Salmonella typhi*.

Typically, the microarray is a linear or two-dimensional array of regions, formed on the surface of a solid support, having a density of discrete regions of at least about $100/cm^2$ and preferably about $1000/cm^2$. The regions in such microarrays have typical dimensions, e.g., diameters, in the range of about 10–250 µm, and are separated from other regions in the array by about the same distance. DNA microarrays can be fabricated by deposition of a set of synthetic oligonucleotides, PCR products, or other forms of genetic material onto the regions of the solid support, such as a silicanated glass slide.

Depending on the size of the genome of the organism of interest, the size of the solid support, and the distance separating the discrete regions, a DNA microarray can be fabricated such that the entire genome is present. Whole genome microarrays containing PCR products derived from the entire genome are fabricated by two general methods. First, if the genome sequence of the organism of interest is available, individual oligonucleotide primer combinations are designed for each coding region in the genome, allowing for the amplification by polymerase chain reaction (PCR) of each gene in independent reactions. The amplification products are then used to fabricate the microarray. If the genome sequence is not available, then a "shotgun" approach is used. In this approach, a library of the genomic DNA is constructed by cloning segments into a vector containing common priming sites adjacent to the cloning site. Each clone from the library is then independently amplified and the amplicons used to fabricate the microarray. Deposition or "printing" of the oligonucleotides onto the solid support can be accomplished by any one of several methods known in the art, such as by an automated arrayer. Regardless of the method that is used to deposit the oligonucleotides onto the solid support, the user should be able to trace the oligonucleotides at a given region back to its original clone.

Phenotypic Characterization of First Sample

There are several acceptable approaches for phenotypically characterizing a sample of a bacterial population including, but not limited to, characterizing the sample based upon serotyping, toxin production, sporulation efficiency, fermentation characteristics, such as food fermentation, and the production of enzymes involved in spoilage or degradation of food sensory characteristics.

Selecting One or More Individuals of First Sample Based Upon Phenotypic Characterization Once the first sample is phenotypically characterized, one or more individuals present in the first sample are selected based upon the phenotypic characterization. The selection is performed such that each individual selected shares the most characters among the other individuals in the sample.

Fabricating Microarray from Each Individual Selected from First Sample

Once one or more individuals of the first sample are selected, a whole genome microarray is prepared from each.

Genotyping Second Sample

Once whole genome microarrays are prepared from each individual selected from the first sample, a second sample of the population is genotyped using each selected individual's microarray as a reference. Preferably, this is performed member-by-member. For each member of the second sample that is genotyped, a predetermined amount of genomic DNA from each of the selected individual(s) and the member is labeled with a fluorescent dye, and then hybridized to the respective microarray(s). Due to complementarity of sequence, the DNA from the selected individual will hybridize to all of the oligonucleotides present in each region of the respective microarray. As such, a different fluorescent dye is used during labeling of the selected individual's DNA and the member DNA.

Following hybridization, fluorescence intensities registered by hybridization of the labeled DNA from the selected individual and the member to each region of the respective microarray are determined by a multicolor, microarray scanner and converted to binary elements or whole integers through image analysis and statistical analysis software. The image analysis software creates an output of the fluorescence intensities, in a spreadsheet file, representing all of the regions of the microarray. For the statistical analysis, it is preferable to use binary conversion to create a bit string representing the pattern of hybridization of the member's DNA to the microarray regions. Binary conversion is performed by comparing the hybridization intensity of each region on different dye channels. If the member DNA contains a hybridizing segment, the ratio of hybridization intensities of the selected individual's DNA and the member's DNA is or is nearly one. If the member DNA lacks the segment, or if the segment is substantially altered, the ratio is much higher. A threshold of ratios is used such that, preferably, a binary bit of 1 is assigned to the region if the ratio of hybridization intensities is >2 standard deviations above the mean, and a binary bit of 0 is assigned to the region if the ratio is <2 standard deviations above the mean. The resulting output file is rendered in text format, although it can also be rendered in spreadsheet format. The output file can contain either converted binary elements or normalized ratios. The statistical analysis software, preferably PERL-based, combines the data from each output file for each member into a composite file, and performs statistical analysis by normalization of the data through mean and median centering of the ratios. Once the composite file is generated, a determination is made as to the genetic relatedness of the members present in the second sample. Such a determination is made by inputting the composite file, preferably containing a bit string corresponding to each member from the second sample, into a separate computer program containing one or more clustering algorithms. Preferably, the clustering program contains both neighbor joining and bootstrap algorithms. The clustering program sorts and groups the data contained in the composite file, while preserving the information concerning the identity of the microarray region corresponding to each bit. The clustering program is directed to render a dendrogram made up of each member of the second sample. Such a dendrogram reveals the relative genetic distance between each member, as well as the existence of genetically related groups or clusters among the members. Phylogeny may also be inferred from the dendrogram. It would be obvious to one skilled in the art that clustering can be performed upon either binary or integer measurements from the array.

Once the members of the second sample are grouped into genetically related groups or clusters, the clustering program is directed to select two such groups or clusters. The clustering program is then directed to identify markers, corresponding to particular microarray regions, that are present in one group or cluster, and absent in another. The program can also be directed to identify markers that are present in at least one member of one group or cluster and absent in all the members of the second group or cluster. Since the information concerning the micorarray region corresponding to each bit is preserved during the sorting and grouping process, microarray regions can be easily identified showing these types of markers. These particular regions can then be identified on the original microarray fluorescence scans.

Also provided is a method for identifying unique bits among a plurality of bit strings including providing a plurality of bit strings wherein each bit string has the same number and position of bits and wherein each bit has a value of 0 or 1, generating a graphical representation—including selectable elements—representing the relatedness of the bit strings, making a selection of a first selectable element, making a selection of a second selectable element, and identifying bits that are present in each bit string represented by the first selectable element and absent in each bit string represented by the second selectable element, or vice-versa. In some embodiments, each bit string represents the genome of an organism and each bit represents that region of a microarray fabricated from oligonucleotide segements of the genome. Also in some embodiments, the relatedness of the bit strings is determined by the commonality of bit values at corresponding positions in the bit strings. In preferred embodiments, the graphical representation is a dendrogram and the selectable elements are leaves and nodes, each leaf representing a single bit string, and each node representing two or more bit strings.

Figure 2:
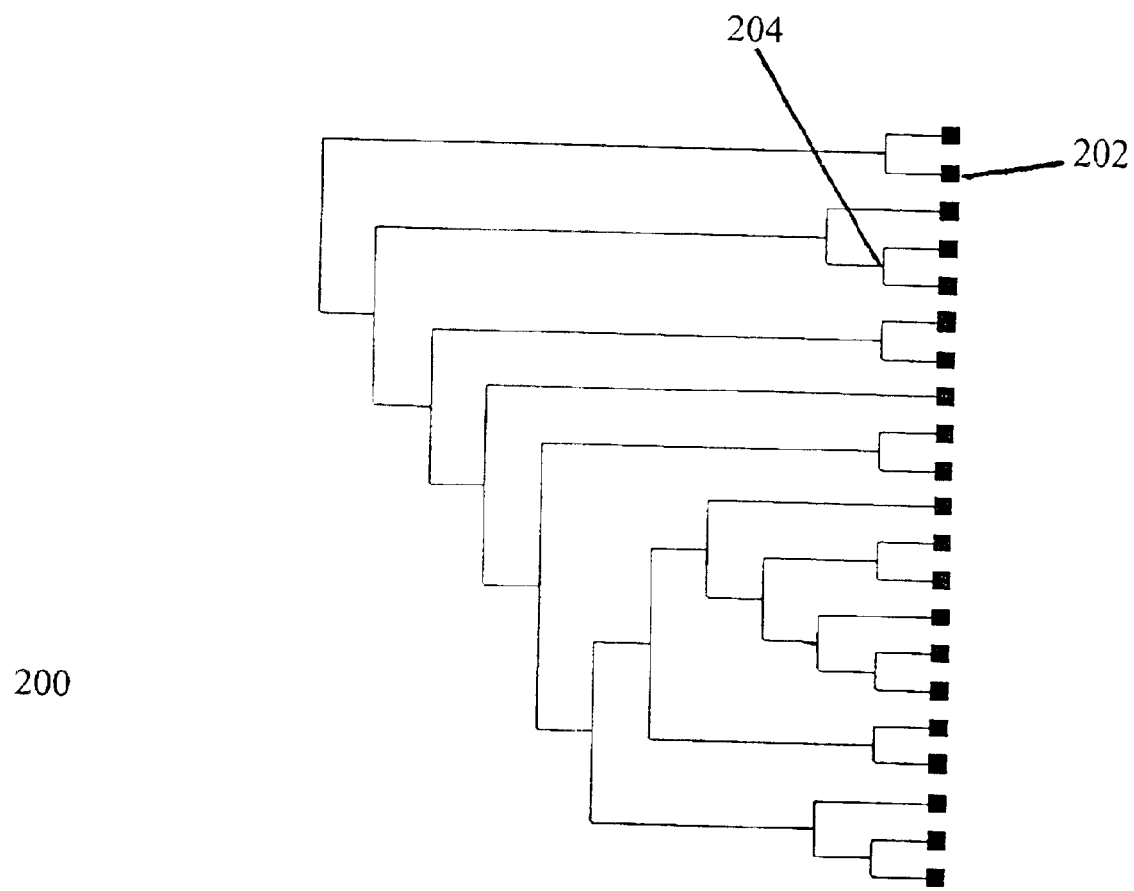
FIG. 2 is a an illustration of a dendrogram generated by the software for identifying unique bits among a plurality of bit strings.

Also provided, as represented in FIGS. 1 and 2, is a computer readable medium having software 100 for identifying unique bits among a plurality of bit strings, including logic configured to provide a plurality of bit strings 102, each string having the same number and position of bits, each bit having a value of 0 or 1, logic configured to generate a graphical representation, including selectable elements, representing the relatedness of the bit strings 104, logic configured to make a selection of a first selectable element 106, logic configured to make a selection of a second selectable element 108, and logic configured to identify bits that are present in each bit string represented by the first selectable element and absent in each bit string represented by the second selectable element 110, or that are absent in each bit string represented by the first selectable element and present in each bit string represented by the second selectable element 112. In one embodiment, the relatedness of the bit strings is determined by the commonality of bit values at corresponding positions in the bit strings. In preferred embodiments, the graphical representation is a dendrogram 200, and the selectable elements are leaves 202 and nodes 204, each leaf representing a single bit string, and each node representing two or more bit strings.

The software 100 can be embodied in any computer-readable medium, or computer-bearing medium, for use by or in connection with an instruction execution system, apparatus, or device, such as a computer-based system, processor-containing system, or other system that may selectively fetch the instructions from the instruction execution system, apparatus, or device and execute the instructions. In the context of this document, a "computer-readable medium" is any means that may contain, store, communicate, propagate, or transport the program for use by or in connection with the instruction execution system, apparatus, or device. The computer readable medium can be, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a RAM (electronic), a read-only memory "ROM" (electronic), an erasable programmable read-only memory (EPROM or Flash memory) (electronic), an optical fiber (optical), and a portable compact disc read-only memory "CDROM" (optical).

The software 100 can also be embodied in at least one computer-readable signal-bearing medium (such as the Internet, magnetic storage medium, such as floppy disks, or optical storage, such as compact disk (CD/DVD), biological, or atomic data storage medium). In yet another example implementation, the computer-readable signal-bearing medium can comprise a modulated carrier signal transmitted over a network comprising or coupled with a diversity receiver apparatus, for instance, one or more telephone networks, a local area network, the Internet, and wireless network. An exemplary component of such embodiments is a series of computer instructions written in or implemented with any number of programming languages. Note that the computer-readable medium can even be paper or another suitable medium upon which the software 100 is printed, as the software 100 can be electronically captured, via for instance optical scanning of the paper or other medium, then compiled, interpreted or otherwise processed in a suitable manner if necessary, and then stored in a computer memory.

Diagnostic Probes and Assays

Once polymorphic markers specific to particular groups or clusters are identified by the methods of the invention, the microarray region information can be used to locate the clone in the original shotgun library. Once the original clone is located, DNA can be extracted therefrom, and used as a probe in a Southern blot to confirm the presence or absence of the particular DNA segment or alterations within it. Once the presence or absence of specific markers is confirmed by Southern blotting, the clone inserts can be sequenced, and used as diagnostic probes in assays for the identification of organisms containing that marker or markers.

The following example is intended to further illustrate the invention and is not a limitation thereon.

EXAMPLE

Fabrication of a *L. monocytogenes* 10403S Shotgun Microarray

To demonstrate the feasibility of using array-based methods to identify genomic diversity in *Listeria monocytogenes* isolates, a shotgun DNA microarray was constructed from strain 10403S. This was accomplished by printing 4,350 PCR amplified inserts from a *L. monocytogenes* 10403S DNA library in duplicate onto silicanated glass slides. To prepare a library as representative as possible, the library was constructed using the TOPO® shot-gun library construction kit (Invitrogen, CA) that shears the genomic DNA with high-pressure air to an average size of 1.5 kilobases. The sheared DNA fragments were then blunt-ended with Klenow and T4-DNA polymerase, followed by dephosphorylation to prevent ligation of non-contiguous fragments in the library. The dephosphorylated DNA fragments were then cloned into the pTopo vector. Individual colonies were immediately transferred to 96-well plates. Amplified inserts from independent clones were analyzed by agarose gel electrophoresis, purified and printed to the array. The average size of the inserts was 1.5 kilobases. Therefore, this microarray provided ca. 1.5-fold redundancy in coverage of the 10403S genome.

Use of the 10403S Genome Microarray as a Reference Array in Genotyping

To demonstrate the potential of shotgun array-based genome comparison to identify genomic divergence, the shotgun array was first used as a reference array to genotype a set of epidemiologically characterized strains. For these pilot studies, 62 different L. monocytogenes strains originating from both clinical and environmental (food) samples were used. DNA was extracted from each strain and 2 $\mu$g was used in a random primer reaction. The reactions were performed in a 50 $\mu$l volume using the Gibco/BRL BIOPRIME® DNA labeling kit (Life Technologies, MD). In each experiment, an independent aliquot of 10403s DNA was random primed using the CY3 dye-labeled nucleotide and the test strain was random primed using the CY5 dye-labeled nucleotide. After labeling, the labeled products were concentrated using a micron 30 filter (Amicon). The entire concentrated products from the CY3 and CY5 labeling reactions were then mixed into 30 $\mu$l of hybridization buffer containing 100 $\mu$g of yeast tRNA and 400 $\mu$g of salmon sperm DNA, layered onto the array, and covered with a coverslip. The hybridization reactions were then placed into individual hybridization chambers and incubated for 3 hours at 65° C. The hybridizations were then washed for 5 minutes each in 1×SSC+0.1% SDS, 0.1×SSC+0.1% SDS, and finally 0.1×SSC. Fluorescence intensities of the array regions were determined using a GSI Lumonics SCA-NARRAY® 3000 multicolor microarray scanner.

In order to examine the relationships of the strains, hybridization intensities registered by hybridization of the CY3-labeled 10403S probes and CY5-labeled test DNA probes at each of the 8,700 different array regions were converted to binary elements. This was conducted by comparing the hybridization intensity of each spot on the CY3 and CY5 channels using ScanAlyze software. This image analysis software provides several methods for generating background-subtracted ratios of fluorescence and outputs the data as a text file.

The FormatALL software, which created composite files of address and background-subtracted ratios from the ScanAlyze files, also normalized the data by mean and median centering each column, corresponding to each individual reference-test strain pair. The software then converted the normalized ratios to binary based on the formula:

X>2 standard deviations=binary 0

X<2 standard deviations=binary 1.

The output file was then formatted by FormatALL for cluster analysis in P.A.U.P. (Phylogenetic Analysis Using Parsimony) 4.0 and MarkFind. Cluster analysis in both P.A.U.P. 4.0 and MarkFind, a software program containing clustering algorithms, such as neighbor joining and bootstrap, that allows for the identification and sorting of polymorphic markers in a population. Marker sorting in MarkFind revaled several loci absent in each clade (Table 1).

TABLE 1

| CLADE | NUMBER OF LOCI ABSENT IN ALL MEMBERS |
|-------|--------------------------------------|
| A | 20 |
| B | 75 |
| C | 42 |
| D | 67 |

REFERENCES

Behr, M. A., M. A. Wilson, W. P. Gill, H. Salamon, G. K. Schoolnik, S. Rane, and P. M. Small. Comparative genomics of BCG vaccines by whole-genome DNA microarray. Science 284:1520–1523 (1999);

Brehm, K., M.-T. Ripio, J. Kreft, and J.-A. Vasquez-Boland. The bvr locus of Listeria monocytogenes mediates virulence gene repression by b-glucosides. Infect. Immun. 181: 5024–5032 (1999);

Brosch, R., J. Chen, and J. B. Luchansky. Pulsed-field fingerprinting of Listeriae: identification of genomic divisions for Listeria monocytogenes and their correlation with serovar. Appl. Environ. Microbiol. 60: 2584–2592 (1994);

Cossart, P., M. F. Vincente, J. Mengaud, F. Baquero, J. C. Perez-Diaz, and P. Berche. Listeriolysin O is essential for virulence of Listeria monocytogenes: direct evidence obtained by gene complementation. Infect. Immun. 57:3629–3636 (1992);

Farber, J. M. and B. E. Brown. Effect of prior heat shock on heat resistance of Listeria monocytogenes in meat. Appl. Environ. Microbiol. 56:1584–1587 (1990);

Farber, J. M. and P. I. Peterkin. Listeria monocytogenes, a food-borne pathogen. Microbiol. Rev. 55:476–511 (1991);

Galliard, J. L., P. Berche, J. Mounier, S. Richard, and P. Sansonetti. In vitro model of penetration and intracellular growth of Listeria monocytogenes in the human enterocytelike cell line Caco-2. Infect. Immun. 55:2822–2829 (1987);

Gellin B. G. and Broome C. V. Listeriosis. JAMA 261(9): 1313–20 (1989);

Gutekunst, K. A., B. P. Holloway, and G. M. Carlone. DNA sequence heterogeneity in the gene encoding a 60-kilodalton extracellular protein of Listeria monocytogenes. Can. J Microbiol. 38: 865–870 (1992);

Graves, L. M., B. Swaminathan, M. W. Reeves, S. B. Hunter, R. E. Weaver, B. D. Pikaytis, and A. Schuchat. Comparison of ribotyping and multi-locus enzyme electrophoresis for subtyping of Listeria monocytogenes isolates. J. Clin. Microbiol. 32: 2936–2943 (1994);

Huillet E, S. Larpin S, P. Pardon, and P. Berche. Identification of a new locus in Listeria monocytogenes involved in cellobiose-dependent repression of hly expression. FEMS Microbiol. Lett. 174:265–72 (1999);

Karaolis, D. K. R. R. Lan, and P. R. Reeves. The sixth and seventh cholera pandemics are due to independent clones separately derived from environmental non-toxigenic non-O1 Vibrio cholerae. J. Bacteriol. 177: 3191–3198 (1995);

Kim J., Nietfeldt J., and Benson A. K. Octamer-based genome scanning distinguishes a unique subpopulation of Escherichia coli O157:H7 strains in cattle. Proc. Natl. Acad. Sci. USA 96(23):13288–93 (1999);

Kroll, R. G., and P. A. Patchett. Induced acid tolerance in Listeria monocytogenes. Lett. Appl. Microbiol 14:224–227 (1992);

Leimeister-Wachter, M., E. Doman, and T. Chakraborty. The expression of virulence genes in *Listeria monocytogenes* is thermoregulated. *J. Bacteriol.* 174:947–952 (1992);

Lockhart, D. J. and E. A. Winzler. Genomics, gene expression, and DNA arrays. *Nature* 405: 827–836 (2000);

Miller, A. J. Combined water activity and solute effects on growth and survival of *Listeria monocytogenes* Scott A. *J. Food Protect.* 55:414–418 (1992);

Mounier, J., A. Ryter, M. Coquis-Rondon, and P. J. Sansonetti. Intracellular and cell-to-cell spread of *Listeria monocytogenes* involves interaction with F-actin in the enterocytelike cell line Caco-2. *Infect. Immun.* 58:1048–1058 (1990);

Musser, J. M. and R. M. Krause in *Emerging Infections*, eds. Krause, R. M. and Faucci, A. Academic, San Diego, Calif. pp. 185–218 (1998);

Musser, J. M. Molecular population genetic analysis of emerged bacterial pathogens: selected insights. *Emerg Infect Dis.* 2:1–17 (1996);

Lawrence J. G. and H. Ochman. Molecular archaeology of the *Escherichia coli* genome. *Proc. Natl. Acad. Sci. USA* 95:9413–7 (1998);

Ochman, H. and I. B. Jones. Evolutionary dynamics of full genome content in *Escherichia coli*. *EMBO* 19:6637–6643 (2000);

Piffaretti, J.-C., H. Kressebuch, M. Aeschenbacher, J. Bille, E. Bannerman, J. M. Musser, R. K. Selander, and J. Rocourt. Genetic characterization of clones of the bacterium *Listeria monocytogenes* causing epidemic disease. *Proc. Natl. Acad. Sci. USA* 86:3818–3822 (1989);

Park, S. F. and R. G. Kroll. Expression of listeriolysin and phosphatidylinositol-specific phospholipase C is repressed by the plant-derived molecule cellobiose in *Listeria monocytogenes*. *Mol. Microbiol.* 8:653–661 (1993);

Perna, N. T., G. Plunkett III, V. Burland, et al. Genome sequence of ehterohemorrhagic *Escherichia coli* O157:H7. *Nature* 409: 529–533 (2001);

Pollack, J. R., C. M. Perou, A. A. Alizadeh, B. Eisen, A. Pergamenschikov, C. F. Williams, S. S. Jeffery, D. Botstein, and P. O. Brown. Genome-wide analysis of DNA copy number changes using cDNA microarrays. *Nature Genetics* 23: 41–46 (1999);

Portnoy, D. A., P. S. Jacks, and D. J. Hinrichs. Role of hemolysin for the intracellular growth of *Listeria monocytogenes*. *J. Exp. Med.* 167:1459–1471 (1988);

Portnoy, D. A., T. Chakraborty, W. Goebel, and P. Cossart. Molecular determinants of *Listeria monocytogenes* pathogenesis. *Infect. Immun.* 60:1263–1267 (1992);

Rasmussen, O. F., T. Beck, J. E. Olsen, L. Dons, and L. Rossen. *Listeria monocytogenes* isolates can be classified into two major types according to the sequence of the listeriolysin gene. *Infect. Immun.* 59:3945–3951 (1991);

Rasmussen, O. F., P. Skouboe, L. Dons, L. Rossen, and J. E. Olsen. *Listeria monocytogenes* exists in at least three evolutionary lines: evidence from flagellin, invasive associated protein, and listeriolysin O genes. *Microbiology* 141: 2053–2061 (1995);

Renzoni, A., A. Klarsfeld, S. Dramsi, and P. Cossart. Evidence that PrfA, the pleiotropic activator of virulence genes in *Listeria monocytogenes*, can be present but inactive. *Infect. Immun.* 65:1515–1518 (1997);

Schena, M., D. Shalon, R. W. Davis, and P. O. Brown. Quantitative monitoring of gene expression patterns with a complementary DNA microarray. *Science* 270: 467–470 (1995);

Seelinger, H. P. R. and Hoehne, K. Serotypes of *Listeria monocytogenes* and related species. *Methods Microbiol.* 13:31–49 (1979);

Sheehan, B., C. Kocks, S. Dramsi, E. Gouin, A. D. Klarsfield, J. Mengaud, and P. Cossart. Molecular and genetic determinants of the *Listeria monocytogenes* infectious process. *Curr. Top. Microbiol.* 192:187–216 (1994);

Schuchat, A., B. Swaminathan, and C. V. Broome. Epidemiology of human listeriosis. *Clin. Microbiol. Rev.* 4:169–183 (1991);

Tilney, L. G. and D. A. Portnoy. Actin filaments and the growth, movement, and spread of the intracellular parasite *Listeria monocytogenes*. *J. Cell. Biol.* 109:1597–1608 (1989);

Verheul, A., E. Glaasker, B. Poolman, and T. Abee. Betaine and L-carnitine transport by *Listeria monocytogenes* ScottA in response to osmotic signals. *J. Bacteriol.* 179:6979–6985 (1997);

Vines, A., Reeves, M. W., Hunter, S., Swaminathan, B. Restriction fragment length polymorphism in four virulence-associated genes of *Listeria monocytogenes*. *Res Microbiol.* 143(3):281–94 (1992);

Wiedmann, M., Bruce, J. L., Keating, C., Johnson, A. E., McDonough, P. L. and Batt, C. A. Ribotypes and virulence gene polymorphisms suggest three distinct *Listeria monocytogenes* lineages with differences in pathogenic potential. *Infect Immun.* 65:2707–2716 (1997);

Wilkins, P. O., R. Bourgeois, and R. G. E. Murray. Psychrotrophic properties of *Listeria monocytogenes*. *Can. J. Microbiol.* 18:543–551 (1972).

While various embodiments of the application have been described, it will be apparent to those of ordinary skill in the art that many more embodiments and implementations are possible that are within the scope of this invention. Accordingly, the invention is not to be restricted except in light of the attached claims and their equivalents.

What is claimed is:

1. A method for identifying polymorphic markers in a population, comprising the steps of:

selecting a first and second individual from a plurality of individuals of the population;

providing a reference genomic DNA microarray;

hybridizing genomic DNA of each of the first and second individuals to the reference microarray;

determining segments of hybridization between the genomic DNA of each of the first and second individuals and the reference microarray;

calculating a hybridization intensity ratio for each hybridized and non-hybridized segment;

converting each intensity ratio into a binary digit consisting of a 0 or 1 bit such that each segment of the reference microarray is represented by a 0 or 1 bit;

compiling data consisting of the numerical elements to produce a bit string for each individual, each bit string having the same total number of bits and each bit having a unique position common to both strings; and analyzing the data to identify patterns of hybridization present in the population, wherein the relatedness of the bit strings is determined by comparing the value of each bit within the bit string of the first individual to the value of each bit within the bit string of the second individual.

2. The method of claim 1, wherein the reference microarray is fabricated from genomic DNA from an individual in the population.

3. The method of claim 1, wherein the step of selecting a first individual involves selecting an individual that shares the most characteristics among other individuals of the same population.

4. The method of claim 3, further comprising the step of labeling the genomic DNA of each selected individual with a fluorescent dye.

5. The method of claim 4, wherein the genomic DNA of each selected individual is labeled a different fluorescent dye.

6. The method of claim 4, wherein the step of determining each segment's hybridization intensity includes determining the fluorescent intensities of the hybridized segments.

7. The method of claim 1, further comprising the step of hybridizing genomic DNA from each of the individuals in the population to the reference microarray to determine genetic relatedness of all of the individuals from the population.

8. The method of claim 1, wherein at least one of the first and second individuals is characterized by genotype, and at least one of the individuals is selected based upon the genotypic characterization.

9. The method of claim 1, wherein at least one of the first and second individuals is characterized by phenotype, and at least one of the individuals is selected based upon the phenotypic characterization.

10. The method of claim 1, further including the step of collecting the bit string for each individual into a composite file.

11. The method of claim 10, wherein the step of analyzing further includes normalizing the data through mean and median centering of each of the hybridization intensity ratios.

12. The method of claim 10, further including the step of preparing a graphical representation for each bit string.

13. The method of claim 1, wherein the population is a bacterial population.

14. The method of claim 13, wherein the bacterial population is selected from the group consisting of *Listeria monocytogenes, Escherichia coli, Lactobacillus casei, Lactobacillus lactus, Salmonella typhimurium, Salmonella entereditis*, and *Salmonella typhi*.

* * * * *